United States Patent [19]
Guern et al.

[11] Patent Number: 5,260,701
[45] Date of Patent: Nov. 9, 1993

[54] BIDIRECTIONAL INDUCTIVE TRANSMISSION OF DATA WITH SLAVE STATION SUPPLIED BY THE MASTER

[75] Inventors: Yves Guern, Jouques; Bruno Dubujet, Aix en Provence; Michel Ayraud, Nice, all of France

[73] Assignee: Société Bertin & Cie, Plasir Cedex, France

[21] Appl. No.: 752,656
[22] PCT Filed: Jan. 18, 1991
[86] PCT No.: PCT/FR91/00026
  § 371 Date: Aug. 22, 1991
  § 102(e) Date: Aug. 22, 1991
[87] PCT Pub. No.: WO91/11063
  PCT Pub. Date: Jul. 25, 1991
[51] Int. Cl.$^5$ .............................. H04Q 1/00
[52] U.S. Cl. .................. 340/825.54; 340/825.72; 455/88
[58] Field of Search ............ 340/825.54, 870.31, 340/870.32, 870.33, 870.34, 870.35, 870.36, 825.72; 128/419 PT, 903; 342/44, 51; 455/41, 83, 89, 88

[56] References Cited

U.S. PATENT DOCUMENTS

| | | | |
|---|---|---|---|
| 4,361,153 | 11/1982 | Slocum et al. | 128/419 PT |
| 4,528,987 | 7/1985 | Slocum | 128/419 PT |
| 4,532,932 | 8/1985 | Batty, Jr. | 128/419 PT |
| 4,543,953 | 10/1985 | Slocum et al. | 128/903 |
| 4,561,443 | 12/1985 | Hogrefe et al. | 128/419 PT |
| 4,700,707 | 10/1987 | Batina et al. | 128/419 PT |
| 4,741,340 | 5/1988 | Batina et al. | |

FOREIGN PATENT DOCUMENTS

0160990 11/1985 European Pat. Off.
2123648A 2/1984 United Kingdom.

OTHER PUBLICATIONS

Patent Abstracts of Japan; vol. 10; No. 197; Jul. 10, 1986 Japanese Pat. Appl'ns No. 6139740(A); 61-39741(A); and 61-39742(A).
IEEE 1987; CH2398-6/37/0000-0394, Numerical Determination of the Performance of Magnetically Coupled Coils in Medical Telemetry Systems, Osama A. Mohammed; pp. 394 to 397.

*Primary Examiner*—John K. Peng
*Assistant Examiner*—Robert Gray
*Attorney, Agent, or Firm*—Watson, Cole, Grindle & Watson

[57] ABSTRACT

A device for the bi-directional transmission of data between a master system and a slave system uses a single transmission antenna and a single reception antenna each tuned to the same frequency; the master system comprises first data transmission circuits for transmitting first data to the slave system by modulating an electromagnetic signal at the frequency; detection circuits for detecting, during the transmission of the electromagnetic signal, variations in electrical characteristics of the master system induced by a modulation of the impedance of the slave system as a function of second data to be transmitted from the slave system to the master system; and restoring circuits for restoring the second data on the basis of the detected variations; and the slave system comprises reception circuits connected to the reception antenna for restoring the first data; a rectifier circuit connected across the reception antenna for rectifying an electrical signal induced in the reception antenna by the electromagnetic signal; a power supply circuit connected to the rectifier circuit for powering the circuits and the loads of the slave system with a DC voltage on the basis of energy from the rectified electrical signal; and a switching circuit connected in series between the rectifier circuit and the power supply circuit to modulate the real part of the impedance of the slave system between a high value and a low value when the switching circuit is driven in its opened and closed position by a control signal representative of the second data.

7 Claims, 3 Drawing Sheets

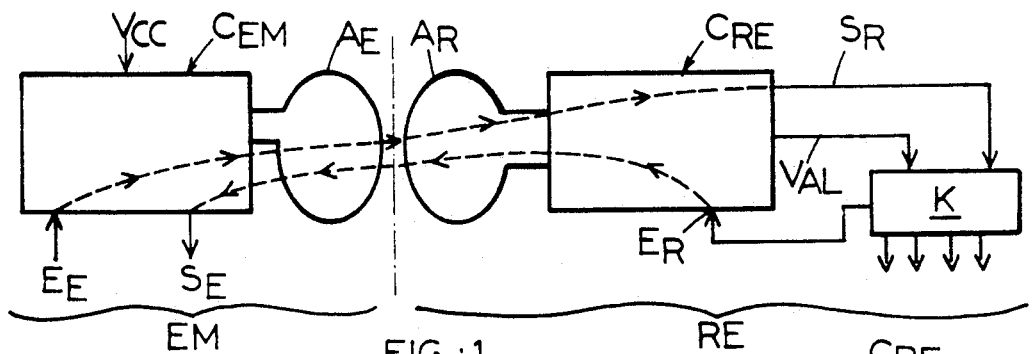
FIG.:1
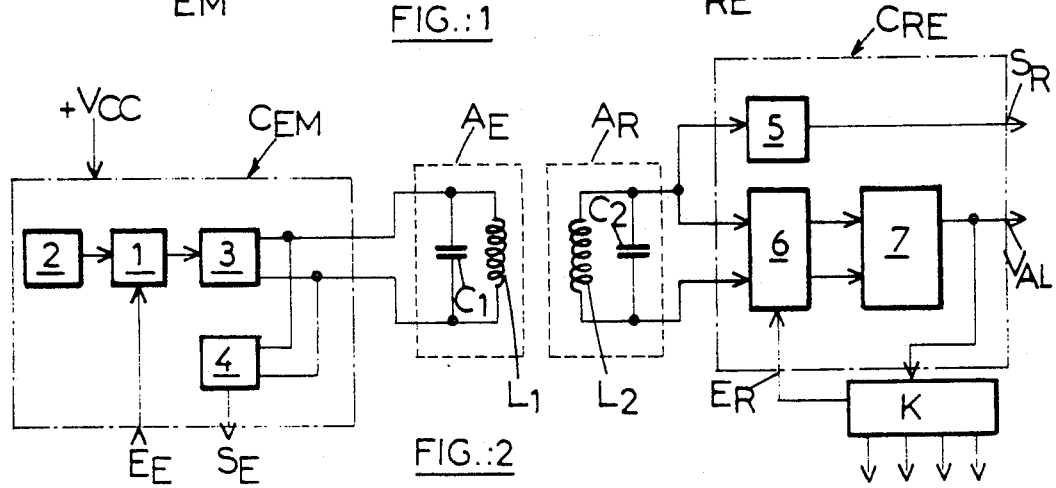
FIG.:2
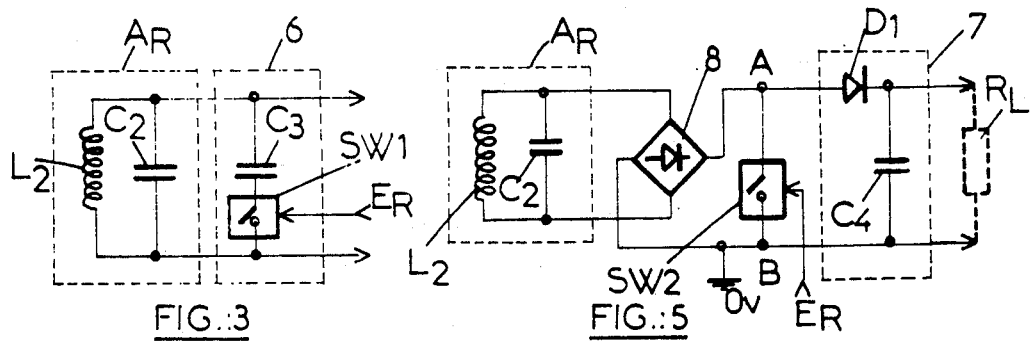
FIG.:3 FIG.:5
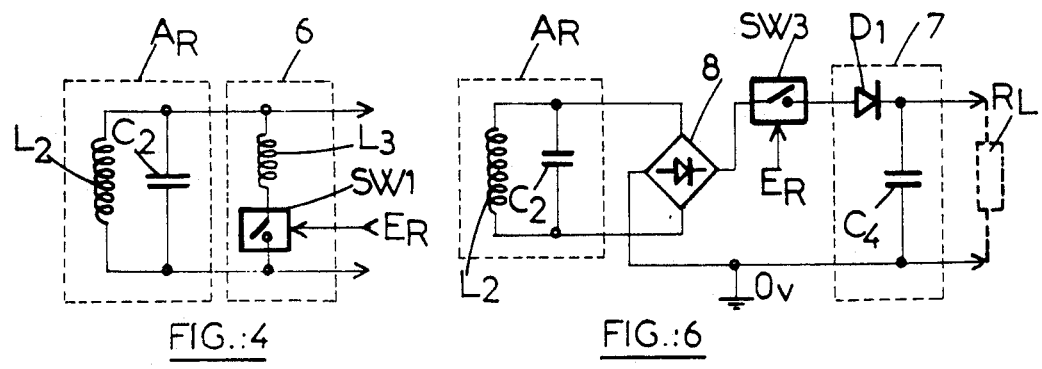
FIG.:4 FIG.:6

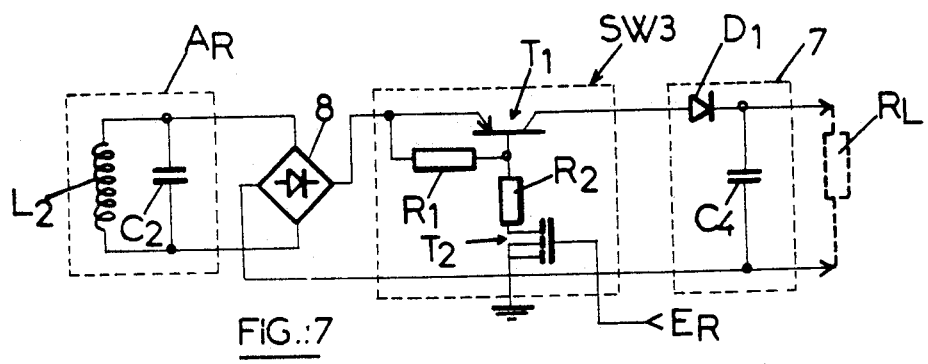
FIG.:7
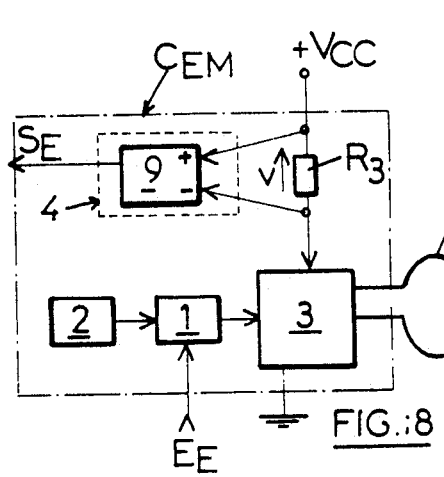
FIG.:8
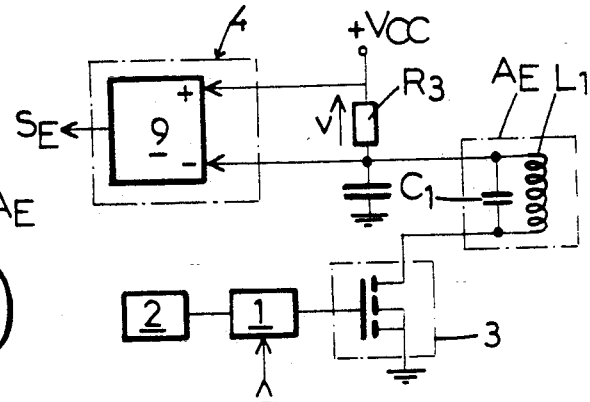
FIG.:9
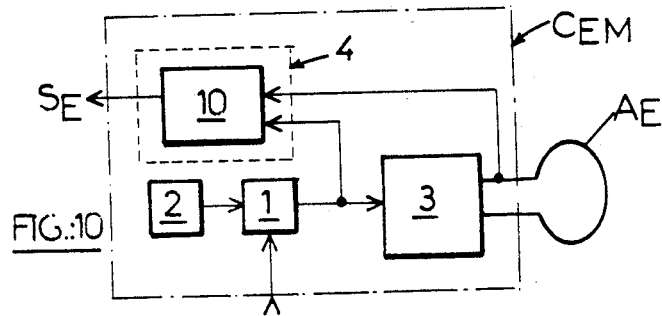
FIG.:10
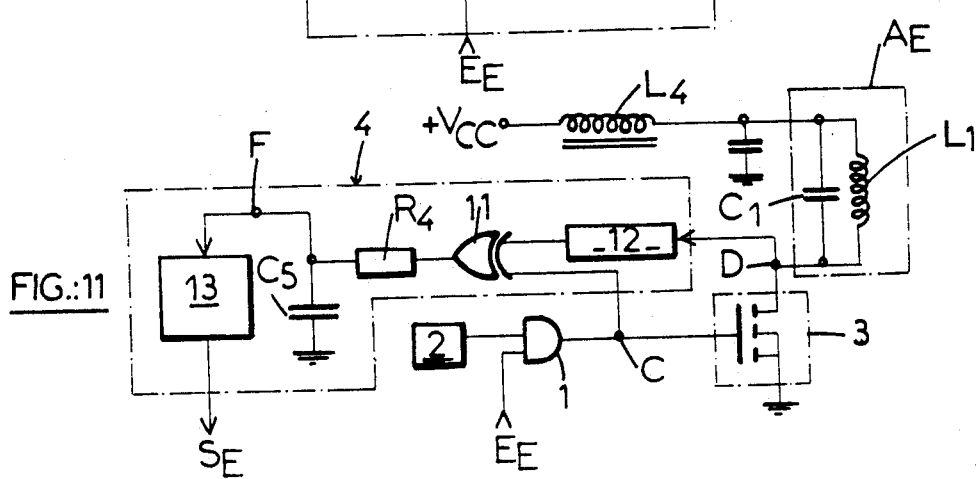
FIG.:11

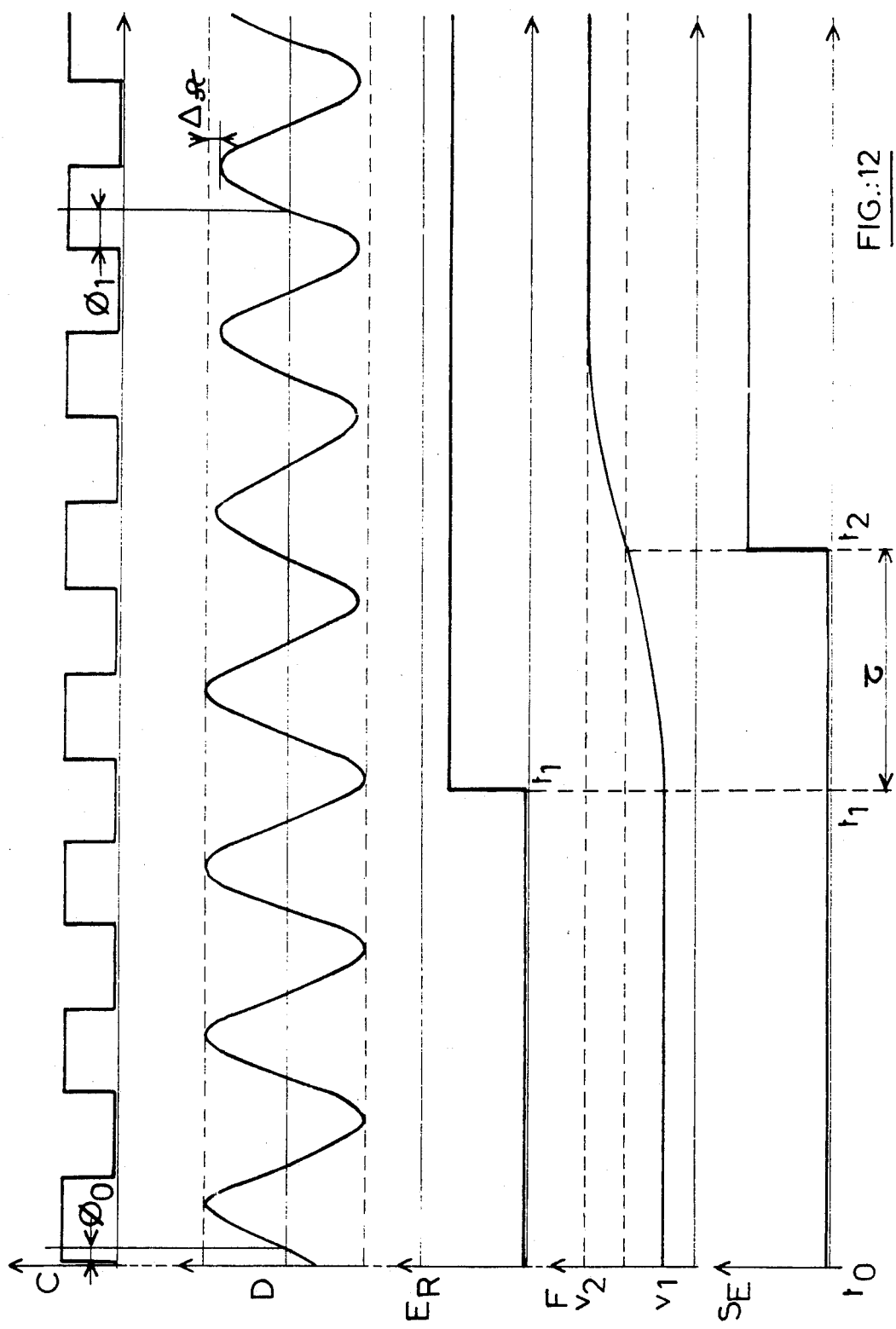
FIG.:12

BIDIRECTIONAL INDUCTIVE TRANSMISSION OF DATA WITH SLAVE STATION SUPPLIED BY THE MASTER

The invention relates to a method of bidirectional transmission of data between a master system (transmitter) and a slave system (receiver) powered on the basis of the electromagnetic energy emitted by the master system, and to a device for implementing this method.

In numerous areas of the art, the need exists to have available such a device, whose slave system, devoid of any self-contained source for supplying electrical energy, is capable of receiving data, of powering electronic circuits or other loads, and of transmitting data to the master system.

Such is the case for example in the area of telemetry, remote control, active electronic devices which can be implanted in a human or animal body, etc., where for reasons of inaccessibility and/or of bulkiness of the slave system, of inadequate reliability and/or lifetime of electric batteries, etc., it is not always possible or desirable to equip the slave system with a self-contained source of electrical energy.

In the remainder of the description "slave system" therefore designates a system comprising at least one antenna and reception circuits and which is entirely dependent on the "master system" for its electrical energy supply, which energy is provided to it in electromagnetic form.

It is already known, in particular in respect of implantable active prostheses, to power a reception module on the basis of the energy radiated by the transmission antenna of a transmission module.

Thus, the document GB-A-2,123,648 describes an implantable prosthesis for biological stimulation comprising a reception antenna which is able to pick up radiation carrying, at one and the same time, control data and the energy required for powering the circuits and loads of the prosthesis. The energy received is stored in a capacitor which, in association with a voltage regulator, serves to supply circuits for demodulating the signal received, for decoding the data carried by this signal, for controlling and supplying the stimulation electrodes, etc. Data transmission takes place solely from the transmitter to the receiver and is therefore unidirectional.

However, it may prove necessary for such a prosthesis or a similar implanted electronic device to also be capable of outside transmission of measurement data on the electrical characteristics of the electrodes, on the state of operation of its electrical circuits, data provided by sensors, etc.

To this end, the document WO 84/01719 describes a device aimed at a similar application, the slave system of which is equipped with a transmission antenna and with circuits for transmitting the said data. The slave system of this device therefore includes both a reception module and a transmission module.

However, as regards the slave system, the not insignificant energy required for the transmission of data by emitting electromagnetic radiation becomes added to the energy consumed by the other circuits and loads which the reception module of the slave system must supply. Now, the instantaneous power extracted by the slave system from the radiation emitted by the master system is relatively low. In practice, this power proves inadequate to supply, at one and the same time, the reception, control and transmission circuits and the electrical loads of the slave system.

For this reason, the document WO 84/01719 provides for equipping the slave system with an accumulator capable of storing the energy picked up by the reception antenna. However, for reasons of bulkiness, weight, safety, reliability or for other reasons the presence of an electric accumulator in the slave system is often unacceptable.

It is moreover known from the document U.S. patent application Ser. No. 4,741,340 to carry out bidirectional transmission of data between a master system and a slave system comprising respectively a transmission antenna and a reception antenna which are tuned to the same frequency f, by modulating the impedance of the slave system, during reception of a data signal emitted by the master system, in accordance with data to be transmitted to the master system. This modulation of the impedance of the slave system is manifested by variations in electrical characteristics of the master system due to the fact that the transmission and reception antennas are coupled. Detection of these variations enables the data transmitted from the slave system to the master system to be restored.

Nevertheless, the device according to the document U.S. patent application Ser. No. 4,741,340 and similar known devices do not allow the slave system to be supplied with electrical energy from the master system.

The aim of the invention is to provide a method and a device allowing, at one and the same time, the bidirectional transmission of data between a master system and a slave system and the powering of the circuits and/or loads of the slave system on the basis of electromagnetic energy emitted by the master system, and this with a single antenna on both the slave system side and the master system side.

To this end, the subject of the invention is a method of bidirectional transmission of data between a master system and a slave system comprising respectively a transmission antenna and a reception antenna which are tuned to the same frequency f, according to which first data are transmitted from the master system to the slave system by modulating an electromagnetic signal at the said frequency f emitted by the master system, the impedance of the slave system is modulated, during transmission of the said electromagnetic signal by the master system, in accordance with second data to be transmitted from the slave system to the master system, variations in electrical characteristics of the master system induced by the said modulating of the impedance of the slave system are detected, and the said second data are restored on the basis of the said detected variations, characterized in that the circuits and/or loads of the slave system are powered on the basis of energy from the said electromagnetic signal of frequency f received by the said reception antenna.

Thus, the method according to the invention utilizes the electromagnetic coupling between single transmission antenna and single reception antenna in order to bidirectionally transmit data from the slave system to the master system, and this without electromagnetic radiation from the slave system, with the result that the bulk of the electromagnetic energy received by the slave system is utilized to power the circuits and/or loads of the latter.

It will be noted that, both on the master system side and the slave system side, a single antenna suffices to transmit data in both directions, as well as the electrical power required by the slave system. A particularly substantial space saving results therefrom on the slave system side.

According to one characteristic of the invention, the variations in the modulus of the impedance of the transmission antenna are detected by detecting variations in the intensity of the direct electric current supplying the transmission circuit of the master system.

According to another characteristic of the invention, variations in the phase angle of the impedance of the transmission antenna are detected by detecting variations in the current/voltage phase lag in the transmission antenna.

The subject of the invention is also a device for implementing the method defined above, in which the slave system includes an electronic switch activated by a signal containing the said second data to be transmitted to the master system and connected into the said slave system in order to vary its impedance depending on whether it is in the open or closed position and the master system includes means of detecting the said variations in electrical characteristics in order to restore the said data, characterized in that the said slave system includes means for converting the energy received by the reception antenna into a DC voltage for supplying the said circuits and/or loads.

The energy required for transmitting data from the slave system to the master system is essentially limited, as regards the slave system, to the consumption of the electronic switch, for example an MOS transistor, which modulates the impedance of the slave system. This energy is therefore very low, and a substantial fraction of the energy picked up by the slave system is still available to supply its other circuits and loads, in particular those formulating the data to be transmitted to the master system.

The device according to the invention opens the way to numerous applications in which recourse to an electric accumulator is excluded for the reasons mentioned earlier. If, for various reasons, an accumulator is still necessary, this device allows considerable improvement in the energy balance.

According to one characteristic of the invention, the said means include a power supply circuit connected to the said reception antenna via a rectifier circuit. Preferably, the power supply circuit includes the combination of a series diode and a parallel capacitor.

According to a first embodiment of the invention in which the imaginary part of the impedance of the slave system is modulated, the said switch forms, with a capacitor or an inductor, a series circuit connected in parallel between the said reception antenna and the said power supply means.

According to a second embodiment of the invention in which the real part of the impedance of the slave system is modulated, the said switch is connected in parallel or in series between the said rectifier circuit and the said power supply circuit.

The detection means can be means of detecting variations in the phase angle or in the modulus of the impedance of the transmission antenna.

Other characteristics and advantages of the invention will emerge from the following description of various embodiments given solely by way of examples and illustrated by the attached drawings, in which:

FIG. 1 is an overall diagram illustrating the method of transmission according to the invention;

FIG. 2 is a block diagram of a transmission device according to the invention;

FIG. 3 is an electrical diagram of a reception antenna associated with a first type of circuit for modulating the imaginary part of the impedance of the slave system;

FIG. 4 is an electrical diagram of a reception antenna associated with a second type of circuit for modulating the imaginary part of the impedance of the slave system;

FIG. 5 is an electrical diagram of a reception antenna associated with a first type of circuit for modulating the real part of the impedance of the slave system;

FIG. 6 is an electrical diagram of a reception antenna associated with a second type of circuit for modulating the real part of the impedance of the slave system;

FIG. 7 is an electrical diagram illustrating a preferred embodiment of the second type of modulating circuit of FIG. 6;

FIG. 8 is an electrical diagram of a first type of circuit associated with the master system of the device for the detection of the data transmitted from the slave system;

FIG. 9 is an electrical diagram illustrating a particular embodiment of the first type of detection circuit of FIG. 8;

FIG. 10 is an electrical diagram of a second type of circuit associated with the master system for the detection of the data transmitted from the slave system;

FIG. 11 is an electrical diagram illustrating a particular embodiment of the second type of detection circuit of FIG. 10; and FIG. 12 is a timing diagram illustrating signals generated in a transmission device equipped with the circuits of FIGS. 7 and 11.

Referring to FIG. 1, the transmission device according to the invention includes a master system EM comprising a transmission antenna $A_E$ and electrical transmission and processing circuits $C_{EM}$ connected to a power source (not shown) which applies a voltage $V_{cc}$ to them. This master system EM has a data input $E_E$ and a data output $S_E$.

A slave system RE, devoid of any connection with the master system EM, includes a reception antenna $A_R$ and electrical reception, power supply and modulation circuits $C_{RE}$ delivering the data received from the master system EM at an output $S_R$, and a DC supply voltage at an output $V_{AL}$. The slave system RE also includes a block K symbolizing electrical circuits such as, for example, circuits for processing the data delivered to the output $S_R$, actuators, circuits supplying electrodes or other loads, sensors gathering data which are applied to an input $E_R$ of the slave system RE in order to be transmitted to the master system EM under conditions which will be described later, etc.

Both antennas $A_E$ and $A_R$ are LC type circuits tuned to the same carrier frequency f and coupled with the result that any modification in the electrical behaviour of one of the systems has repercussions on the other system. In operation, the master system EM emits on the frequency f which is modulated, for example in all-or-nothing mode, by the data applied to the input $E_E$. The signal coming from the transmission antenna $A_E$ and picked up by the reception antenna $A_R$ carries, at one and the same time, these data and the energy required for supplying the slave system RE. The electrical circuits $C_{RE}$ include conventional reception and power supply circuits making it possible, on the one hand, to extract and shape the data transmitted by the master system EM, the routing of which is symbolized by the dashed line stretching between the input $E_E$ and the output $S_R$ and, on the other hand, to convert the energy received by the antenna $A_R$ into a DC supply voltage $V_{AL}$ which supplies all the slave system RE side circuits.

The data applied to the input $E_R$ by the circuits of the block K are transmitted to the master system EM by virtue of a modulation of the impedance of the slave system RE which takes place while the master system EM is emitting. This data transmission is symbolized by the dashed line which stretches between the input $E_R$ of the slave system RE and the output $S_E$ of the master system EM. The procedure which governs this transmission is as follows: as a variation in coupling exists between the master system and the slave system, the impedance $Z_E$ of the transmission antenna $A_E$, seen by the master system EM, is of the form:

$$Z_E = Z_O + \frac{M^2 \omega^2}{Z_R}$$

where
- $Z_O$ represents the impedance of the transmission antenna $A_E$ in the case of a slave system placed infinitely far away,
- $Z_R$ represents the impedance of the slave system RE (reception antenna $A_R$ and associated circuits);
- M represents the coupling coefficient between the transmission antenna and the reception antenna, which coefficient depends on the geometrical characteristics of the antennas (diameter, separation) and on the quality of coupling of these antennas, and
- $\omega$ represents the angular frequency of the frequency emitted by the master system EM.

Consequently, by modulating the impedance $Z_R$, variations, which may be detected at master system EM level, are induced in the impedance $Z_E$, permitting the data which were applied to the input $E_R$ of the slave system RE to be restored.

The method of transmission just described thus permits bidirectional transmission of data between the master system and the slave system on a single frequency, and this by means of a single antenna both on the master system side and the slave system side. Consequently, space is thereby saved on both master system and slave system side, and power is saved as regards the slave system since, as will emerge from the following description, the energy required to modulate the impedance of the slave system is extremely low. This point is very important since the slave system draws energy only from the signal received from the master system and this energy must preferably be utilized to supply a certain number of electrical loads such as actuators, sensors, various electronic circuits, etc. which are associated with the slave system.

Referring to FIG. 2, the reception and processing circuits $C_{EM}$ include a modulator 1 which modulates the constant-frequency signal delivered by a driving oscillator 2 in accordance with a modulating signal which is applied thereto at the input $E_E$. The modulation is preferably of the all-or-nothing type, that is to say the signal from the driving oscillator 2 is applied by the modulator 1 to the input of a power amplifier 3 (power required for supplying the slave system) when the modulating signal is in a high state and no signal is applied to the input of the power amplifier 3 when the modulating signal is in the low state, or vice versa. The transmission antenna $A_E$ is of conventional type having inductance $L_1$ and capacitance $C_1$.

The circuits $C_{EM}$ are completed with a circuit 4 for detecting or measuring variations in an electrical characteristic which are induced in the master system EM by the modulating of the impedance of the slave system. The characteristic whose variations are detected may be a quantity representing the modulus or the phase angle of the impedance of the transmission antenna $A_E$.

On the slave system side, the antenna $A_R$ is also a tuned antenna of the type having inductance $L_2$ and capacitor $C_2$. The circuits $C_{RE}$ include conventional electronic reception circuits 5 which demodulate and shape the signal received by the reception antenna $A_R$ and deliver to the output $S_R$ the data transmitted by the master system EM.

The antenna $A_R$ is also coupled to an impedance-modulating circuit 6 which receives the data to be transmitted to the master system EM on its input $E_R$. The circuits $C_{RE}$ are completed with a conventional power supply circuit 7 which converts the energy received by the reception antenna $A_R$ into a DC supply voltage $V_{AL}$ which serves to supply the various circuits or loads K connected to the slave system, in particular sensors applying data to the input $E_R$ of the modulating circuit 6.

The impedance $Z_R$ of the slave system RE, referred to the transmission antenna $A_E$, is of the form $R+jX$ where R represents the real part of this impedance and X its imaginary part. The real part R consists essentially of the losses due to the fact that the slave system consumes energy and exhibits a certain equivalent resistance in relation to the master system. The imaginary part X is practically constant for a given carrier frequency and given antenna tuning. Hence, in order to modulate the impedance $Z_R$, it is possible to vary its real part and/or its imaginary part.

The diagram of FIG. 3 represents a first circuit associated with the reception antenna $A_R$ for varying the imaginary part X of the impedance $Z_R$. This first circuit includes, in parallel with the inductor $L_2$ and the capacitor $C_2$, the combination in series of a capacitor $C_3$ and an electronic switch SW1 activated by the data applied to the input $E_R$ of the slave system.

Thus, when the switch SW1 is open, the impedance of the slave system RE is not affected, when this switch is closed the capacitor $C_3$ becomes connected in parallel with the capacitor $C_2$ and the imaginary part X of the impedance $Z_R$ becomes modified. The data applied to the control input $E_R$ of the switch SW1 consist of a signal having two states, of which the one enforces the closing of the switch and the other its opening.

The modulating circuit 6 of FIG. 4 differs from that of FIG. 3 solely in that the capacitor $C_3$ is replaced by an inductor $L_3$. As in the case of FIG. 3, bringing the inductor $L_3$ into circuit or removing it therefrom has the effect of modifying the imaginary part of the impedance $Z_R$.

The circuits of FIGS. 3 and 4 offer the possibility of greatly varying the imaginary part X of the impedance $Z_R$ and of thus facilitating measurement of the variations in the impedance $Z_E$ of the transmission antenna. On the other hand, the switch SW1, for example a transistor, must be in a position to switch over to an AC signal, have a very small stray capacitance and be capable of withstanding high voltages of the order of, for example, 100 volts, since it is frequently necessary to make use of such high voltages in order to operate electronic circuits or loads associated with the slave system.

Another possibility illustrated by FIGS. 5 and 6 consists in varying the real part R of the impedance $Z_R$.

In FIG. 5, the antenna $A_R$ is connected to the power supply circuit 7 via a conventional rectifier bridge 8. The circuit 7 supplies all the electronic circuits, sensors and other electrical energy-consuming elements (block K), symbolized by a load $R_L$ in the figure. This circuit 7 consists conventionally of a diode $D_1$ arranged in series in one of the output branches of the rectifier bridge 8 and of a storage capacitor $C_4$ connected, between the output branches of the bridge, downstream of the diode $D_1$. An electronic switch SW2 is also connected between the output branches of the rectifier bridge 8, between the latter and the diode $D_1$. The control electrode of the switch SW2 constitutes the input $E_R$ to which the data to be transmitted to the master system EM are applied.

In this setup, the modulation performed by means of the switch SW2 has the effect of influencing the DC consumption of the slave system. The modulating circuit has the advantage of being simple since it switches only DC voltages exhibiting a reference relative to earth (0 volts). In operation, when the switch SW2 is closed, the impedance which is seen between its terminals A and B is low. The diode $D_1$ prevents the capacitor $C_4$ from completely discharging across the switch SW2. When the latter is open, the capacitor $C_4$, which discharged slightly into the load $R_L$, recharges whilst offering a low impedance. Consequently, the real part R of the impedance $Z_R$ varies only weakly, especially in the transient regime, and it is relatively tricky to ensure detection of the variations induced on the master system side.

From this point of view, the circuit of FIG. 6 gives greater satisfaction. This circuit differs from that of FIG. 5 in that the switch SW3 is connected, not between the output branches of the rectifier bridge 8, but in series between one of the output branches of the rectifier bridge 8 and the anode of the diode $D_1$, the other branch of the dividing bridge being the one which is connected to earth. As in the case of FIGS. 3 to 5, the control electrode of the switch SW3 constitutes the data input $E_R$ of the slave system.

In operation, when the switch SW3 is open, the real part R of the impedance $Z_R$ represents the losses in the antenna $A_R$ and R is therefore high. When the switch SW3 is closed, the real part R is represented by the placing in parallel of the ohmic losses in the antenna with the load $R_L$ representing all the energy-consuming elements. The real part R is therefore small and it is further reduced during the transient periods during which the capacitor $C_4$ must recharge.

The circuit of FIG. 6 therefore makes it possible to induce sizable variations in the real part R of the impedance $Z_R$ and thus to easily detect the induced variations in the impedance $Z_E$ of the transmission antenna $A_E$. Against this, the electronic switch SW3 becomes referenced relative to the output voltage of the rectifier, which leads to utilizing a PNP or PMOS transistor which is more difficult to drive than in the case of FIG. 5.

FIG. 7 shows a particular embodiment of the switch SW3 of FIG. 6. This switch includes a PNP transistor $T_1$ whose emitter is connected to the output branch of the rectifier bridge 8 delivering the supply voltage, and whose collector is connected to the anode of the diode $D_1$. The emitter of the transistor $T_1$ is connected to its base by a resistor $R_1$. The base of the transistor $T_1$ is connected to the other output branch (earth) of the rectifier bridge 8 via a resistor $R_2$ and via the drain-source path of a MOSFET-type transistor $T_2$. The grid of the transistor $T_2$ constitutes the input $E_R$ to which the data to be transmitted from the slave system to the master system are applied.

In operation, when the signal applied to the grid of the transistor $T_2$ through the input $E_R$ is at the low level, the transistor $T_2$ is blocked, the same being true of the transistor $T_1$ whose base is at the same potential as the emitter. The switch SW3 is therefore open. When a high level is applied to the input $E_R$, the transistor $T_2$ is rendered conductive and unblocks the transistor $T_1$ whose base becomes negatively biased relative to its emitter. The switch SW3 is then in the closed position.

The block diagram of FIG. 8 illustrates a first type of circuit 4 for detecting variations in the impedance $Z_E$ which are induced by the modulating of the impedance $Z_R$. The operation of this detection circuit 4 is based on the fact that when the impedance $Z_R$ is modified, its modulus $/Z_R/ = \sqrt{R^2 + X^2}$ is modified, and the antenna $A_R$ is mistuned. Consequently, the DC electrical consumption of the transmission circuit of the master system EM is modified since the energy emitted by the transmission antenna $A_E$ is partially reflected by the reception antenna $A_R$. In this detection mode, the amplifier 3 which drives the transmission antenna $A_E$ must be of class B or class C type so as to obtain electrical consumption over the DC supply $+V_{cc}$ which varies with the impedance $Z_E$.

The detection circuit 4 consists of a differential amplifier 9 which is connected to the terminals of a resistor $R_3$ through which passes the current $I_{cc}$ for supplying the power amplifier 3. The voltage measured across the terminals of the resistor $R_3$ by the differential amplifier 9 is representative of this current $I_{cc}$. The current $I_{cc}$ itself varies with the modulus of the impedance $Z_R$ and, consequently the differential amplifier 9 delivers to the output $S_E$ a signal which is the image of the data applied to the input $E_R$ of the master system. If necessary, the signal delivered by the differential amplifier 9 can be shaped by conventional circuits (not shown).

FIG. 9 illustrates a particular embodiment of the circuit of FIG. 8, in which the amplifier 3 consists of a MOSFET transistor whose grid is controlled by the modulator 1 and whose drain-source path is connected between one of the terminals of the antenna $A_E$ and earth, the other terminal of the antenna being connected to the positive pole $+V_{cc}$ of the supply source via the resistor $R_3$. In this mode of detecting variations in the impedance $Z_E$, the amplifier 3 must have the lowest possible no-load consumption so as to exhibit a good signal/noise ratio.

Another mode of detecting variations in impedance induced at transmission antenna $Z_E$ level consists in detecting the variations in the current/voltage phase lag in the transmission antenna $A_E$. Indeed, when the real part R or the imaginary part X of the impedance $Z_R$ are varied, the phase angle thereof $\Phi = \arctan \frac{X}{R}$ varies.

The block diagram of FIG. 10 illustrates a means of implementing this mode of detection. In this figure the detection circuit 4 consists of a phase detector or phase meter 10 both inputs of which are connected to the input and to the output respectively of the power amplifier 3. Indeed, for an amplifier device, there is a relationship between the input voltage and the output voltage and this relationship normally depends on the nature of the load. Consequently, the input/output phase lag of the amplifier 3 mirrors the current/voltage phase lag in the antenna $A_E$. At its output $S_E$ the phase detector 10 produces a signal representative of this phase lag and, consequently, of the signal applied to the input $E_R$ of the slave system RE.

FIG. 11 illustrates a particular embodiment of the circuits of FIG. 10. The modulator 1 consists of an AND gate which receives the carrier delivered by the driving oscillator 2 at one of its inputs, and the two-state signal to be transmitted to the slave system at its other input $E_E$. When this signal is at the high level, the AND gate applies the carrier to the power amplifier 3 and when it is at the low level the AND gate is blocked and the carrier is not transmitted. The power amplifier 3 consists of a MOSFET transistor whose grid C is connected to the output of the AND gate, whose drain D is connected to one of the terminals of the transmission antenna $A_E$ and whose source is connected to earth. The other terminal of the antenna $A_E$ is connected to the positive pole $+V_{cc}$ of the supply source via a choke $L_4$.

The phase detector 10 includes an EXCLUSIVE OR gate 11 one of the inputs of which is connected to the grid C of the transistor 3 and the other input of which is connected to the drain D of this transistor via a peak-limiter 12. Indeed, detection of the phase lag takes place between grid and drain of the transistor since the voltage gain of such a (common source) setup equals $-gmZ$.

The output from the gate 11 drives the input of an RC circuit which includes a series resistor $R_4$ and a capacitor in parallel $C_5$. The output E of the RC circuit is connected to the input of a shaping circuit 13 whose output constitutes the data output $S_E$ of the master system EM.

The operation of the circuit of FIG. 11 is illustrated by the timing diagram of FIG. 12 in which:
 the signal C is that applied to the grid of the transistor 3 of FIG. 11 (point C);
 the signal D is that present at the drain of the transistor 3 of FIG. 11 (point D);
 the signal E is that present at the output of the circuit $R_4$-$C_5$ of FIG. 11 (point E);
 the signal $S_E$ is that present at the output of the shaping circuit 13 of FIG. 11;
 the signal $E_R$ is that applied to the grid of the transistor $T_2$ of FIG. 7.

Between the instants $t_0$ and $t_1$, the input $E_R$ (grid F of the transistor $T_2$) is at the low level and the impedance $Z_R$ is not modified. Consequently, the phase lag (relative offset of the zero crossings) between the square-wave signal C and the alternating signal D is limited to a small constant value $\Phi_0$ and the signal at the point F remains at the low level by virtue of the time constant of the circuit $R_4C_5$ which smooths the short-duration pulse (not shown) generated at the output of the EXCLUSIVE OR gate 11 owing to the constant phase lag $\Phi_0$. When, at the instant $t_1$, the input $E_R$ changes to the high level, the phase lag between the signals present at the points C and D changes gradually from $\Phi_0$ to $\Phi_1$ and the output signal F from the circuit $R_4C_5$ changes gradually from a voltage $V_1$ to a voltage $V_2$. When at the instant $t_2$ the signal F reaches the threshhold $V_2$ of the shaping circuit 13, and the output $S_E$ from the latter changes to the high level.

The interval $t_1$-$t_2$ represents a response time $\tau$ which depends on the frequency f of the carrier and on the quality factor Q of the transmission and reception antennas and which limits the maximum rate at which data can be transmitted from the slave system to the master system. In practice, the useful pass band stretches from zero to approximately a third of the carrier frequency.

When the signal $E_R$ changes back to the low state, the phase lag changes back gradually from $\Phi_1$ to $\Phi_0$ and $S_E$ changes back to the low state after the response time $\tau$.

By modulating the impedance of the slave system RE during the phases of transmission of a signal by the master system, it is thus possible to very simply recover data at the master system EM level. Different modes of coding the information transmitted from the master system EM to the slave system RE and, in the opposite direction, from the slave system to the master system, can be utilized. Thus, the data can for example be coded with variable-width pulses for the transmission of analog data, or with constant-width pulses for the transmission of digital data. The scope of the present invention does not encompass a description of the various possible modes of coding, and which are well known to specialists in the art of data transmission.

The transmission device according to the invention may advantageously be applied to active electronic devices which can be implanted in a human or animal body. The slave system RE then constitutes the implanted electronic device which can be interrogated and/or activated on request, in order for example to control the duration and intensity of the current provided to one or more stimulation electrodes. The data transmitted to the master system by the implanted electronic device may consist, for example, of inter-electrode impedance measurements using a conventional impedance-measuring circuit which it is not necessary to describe in detail here. These data may also come from various implanted sensors and be transmitted serially to the master system. As a variant, the sensors may be interrogated selectively.

The various modes of modulating the impedance $Z_R$ differ in efficiency depending on the values of f and of Q. Thus, for example, the mode of modulation illustrated by FIG. 3 is relatively inefficient at a high frequency f since the variation in the impedance $Z_R$ introduced by connecting the capacitor $C_3$ in parallel with the capacitor $C_2$ is low. This mode of modulation is by contrast efficient at low frequency f, but on the other hand introduces considerable mismatching of the antenna $A_R$. The frequency f of the carrier will generally be between 100 KHz and 100 MHz, although the device according to the invention can operate at frequencies lying outside this bracket.

Knowing that the data throughput from the slave system to the master system is also a function of the frequency f of the carrier and of the quality factor Q of the antennas, the choice of a mode of modulation for a given application involves a compromise between the outgoing and incoming data throughputs and the efficiency of the transfer of energy to the slave system and can be made by the specialist in radio applications relying on applying his everyday knowledge.

It is self-evident that the embodiments described are merely examples and could be modified by substituting technical equivalents without departing from the scope of the invention.

We claim:

1. A device for the bi-directional transmission of data between a master system and a slave system, comprising:

a single transmission antenna and a single reception antenna each tuned to the same frequency;

said master system comprises first data transmission means for transmitting first data to said slave system by modulating an electromagnetic signal at said frequency; detection means for detecting, during said transmission of said electromagnetic signal, variations in electrical characteristics of said master system induced by a modulation of the impedance of said slave system as a function of second data to be transmitted from said slave system to said master system; and restoring means for restoring said second data on the basis of said detected variations; and said slave system comprises reception circuit means connected to said reception antenna for restoring said first data; a rectifier circuit connected across said reception antenna for rectifying an electrical signal induced in said reception antenna by said electromagnetic signal; a power supply circuit connected to said rectifier circuit for powering the circuits and the loads of said slave system with a DC voltage on the basis of energy from said rectified electrical signal; and a switching circuit connected in series between said rectifier circuit and said power supply circuit to modulate the real part of the impedance of said slave system between a high value and a low value when said switching circuit is driven in its opened and closed position by a control signal representative of said second data.

2. A device according to claim 1, wherein said power supply circuit includes the combination of a series diode and a parallel capacitor.

3. A device according to claim 1, wherein said detection means include means of detecting variations in the electrical power consumed by said transmission antenna.

4. A device according to claim 1, wherein said detection means include means of detecting variations in the current/voltage phase lag in the transmission antenna.

5. A device according to claim 1, wherein said slave system constitutes an active electronic device which can be implanted in a human or animal body.

6. A device according to claim 1, wherein said switching circuit comprises a first transistor having an emitter-collector path connected in series between said rectifier circuit and said power supply circuit; a first polarization resistor connected between the base of said first transistor and said rectifier circuit; and a second polarization resistor connected between said base and ground.

7. A device according to claim 6, wherein said switching circuit further comprises a second transistor having a drain-source path connected in series between said second resistor and ground and receiving on the grid thereof said control signal.

* * * * *